United States Patent [19]

Reuter et al.

[11] Patent Number: 5,446,063
[45] Date of Patent: Aug. 29, 1995

[54] ANESTHETIC COMPOSITIONS

[75] Inventors: Gerald L. Reuter, Plattsburgh, N.Y.; Maureen M. Harrison; Mark E. Coons, both of St. Albans,, Vt.

[73] Assignee: American Home Products Corporation, Madison, N.J.

[21] Appl. No.: 667,234

[22] Filed: Mar. 8, 1991

Related U.S. Application Data

[63] Continuation of Ser. No. 428,488, Oct. 31, 1989, abandoned, which is a continuation of Ser. No. 925,844, Oct. 30, 1986, abandoned.

[51] Int. Cl.$^6$ .................. A61K 31/24; A61K 31/245; A61K 9/06; A61K 9/10
[52] U.S. Cl. .................... 514/535; 514/536; 514/844; 514/847; 514/938; 514/944; 514/969
[58] Field of Search ................ 514/535, 536

[56] References Cited

U.S. PATENT DOCUMENTS

| 2,340,776 | 2/1944 | Stamlowsky | 514/536 |
| 4,052,513 | 10/1977 | Kaplan et al. | 424/310 |
| 4,241,048 | 12/1980 | Durbak et al. | 424/45 |
| 4,344,965 | 8/1982 | Stone | 424/310 |
| 4,600,575 | 7/1986 | Lin et al. | 424/45 |
| 4,600,575 | 7/1986 | Lin et al. | 514/536 |

Primary Examiner—Dale R. Ore
Attorney, Agent, or Firm—J. W. Routh

[57] ABSTRACT

Novel topical anesthetic compositions containing high concentrations of benzocaine in a micronized powder form suspended in an emollient vehicle.

7 Claims, No Drawings

ANESTHETIC COMPOSITIONS

This is a continuation of application Ser. No. 07/428,488 filed on Oct. 31, 1989, now abandoned, which is a continuation of application Ser. No. 925,844, filed Oct. 30, 1986, now abandoned.

BACKGROUND OF THE INVENTION

1. Field of The Invention

This invention relates to novel topical anesthetic compositions containing high concentrations of benzocaine in a micronized powder form. More particularly this invention relates to novel anesthetic compositions for topical administration having a smooth feeling when applied to the skin and remaining smooth after drying and comprising an emollient vehicle having suspended therein micronized benzocaine.

2. Description of Related Art

An aerosol anesthetic composition comprising high concentrations of benzocaine is described in U.S. Pat. No. 4,600,575. That patent and the patents discussed therein, particularly U.S. Pat. No. 4,052,513, all disclose benzocaine compositions wherein the benzocaine is dissolved in a suitable solvent and incorporated into an aerosol system or incorporated into an ointment, lotion, spray, gel, etc. As explained in patent 4,600,575 increasing the concentration of benzocaine, however, had to be balanced against the increasing probability of benzocaine precipitation, particularly at low temperatures. Benzocaine precipitation forms relatively large crystals which, when formed in situ in an ointment or lotion, for example, produce a gritty feeling when applied to the skin, or clog spray equipment when incorporated in a spray.

SUMMARY OF THE INVENTION

According to this invention an elegant anesthetic composition is provided for topical administration containing high concentrations of benzocaine substantially in solid micronized form dispersed or suspended in an emollient vehicle. The anesthetic compositions have a benzocaine concentration of at least about 2% and up to about 20% by weight, have a smooth feeling when applied to the skin, and leave a smooth feeling when dried. Although not desiring to be bound by any theory, it is thought that some or all of the benzocaine may be complexed with the warm natural oils present at the skin surface.

Details of The Invention

Benzocaine useful in forming the anesthetic compositions of this invention can be obtained commercially in micronized form or can be micronized in suitable equipment after purchase. By micronized is meant finely divided or pulverized into particles a few microns in diameter such as particles passing through a 170 standard (U.S. Series) sieve. Preferably the average particle size is not greater than 20 microns with not more than 5% of the particles between 50 and 200 microns.

The emollient vehicle can be composed of the usual constituents so long as they do not dissolve the benzocaine to any great extent. For example, the benzocaine solubility in the emollient vehicle should not be greater than about 2% by weight of benzocaine since the problem of recrystallization of benzocaine from the emollient vehicle particularly on aging might occur and, for example, the lotion would impart a gritty feeling to the skin when applied. Suitable constituents of the emollient base are lanolin and lanolin alcohol fractions, cetyl alcohol, lactates, glycerin, glyceryl stearates, glyceryl oleates, mineral oil, petrolatum, paraffin, beeswax and the like. The components of the emollient vehicle can be appropriately selected to provide a lotion, ointment or gel.

Various optional ingredients may be included in the formulation so long as they do not dissolve the benzocaine to any great extent. Such optional ingredients include perfumes; preservatives, e.g. parabens; antiseptics, e.g. zinc oxide micronized; pigments; humectants, e.g. glycerin; antioxidants; chelating agents, e.g. disodium EDTA; stabilizers, e.g. xanthan gum, carboxyvinyl polymers carboxymethyl cellulosics; dyes; antifoam agents; viscosity control agents, e.g. smectite minerals; trolamine; healing agents, e.g. skin respiratory factor, as well as any other class of material whose presence may be cosmetically or otherwise desirable.

The remainder of the composition would consist essentially of water which would generally be in the range of 30–90 percent, with a preferred range of 40–70 percent.

The pH of the composition is preferably in the range of 5 to 7.5 since benzocaine is less soluble in this environment.

The preparation of the formulations in accordance with the invention is illustrated in the following examples.

EXAMPLE 1

The following ingredients were incorporated into the anesthetic lotion of this invention.

| Ingredient | Weight % |
| --- | --- |
| Benzocaine, USP Micronized | 8 |
| Fractionated Lanolin Alcohols | 0.1 |
| Glycerin, USP | 1.5 |
| Glyceryl Monostearate | 2.5 |
| Menthol, USP | 0.5 |
| Methylparaben, NF | 0.2 |
| Propylparaben, NF | 0.025 |
| Simethicone, USP | 0.2 |
| Trolamine, NF | 0.104 |
| Aloe Vera Gel | 0.1 |
| Carbomer 934 P brand of carboxy-vinyl polymer | 0.49 |
| Water q.s. to | 100% |

The ingredients were admixed in accordance with the following procedure.

Approximately half of the purified water was placed into a jacketed stainless steel container equipped with a propeller type stirrer and heated to about 80° C. The methylparaben and propylparaben were added and mixed until the mixture was clear. Using high speed mixing the carboxy-vinyl polymer was added and then mixing slowly the simethicone was added.

The glyceryl monostearate was of the self emulsifying type and was melted in a separate container and then added to the above admixture with high mixing until homogeneous. The fractionated alcohol fraction, Solulan 16, was added and dispersed by mixing. The batch was brought to a Temperature of 35°–40° C. and the glycerin and aloe were added and mixed until dispersed. The menthol which had been micronized was added with mixing until dispersed and the micronized benzocaine was added and dispersed at a temperature of 22°–27° C. The trolamine was then added and mixed until uniform and then the remainder of the water was added and mixed until the batch was uniform. The batch was then homogenized at 900 psig and filled into polypropylene bottles. This lotion formulation containing 8% benzocaine is useful for application to sunburn, minor scrapes and bruises, insect stings and bites, poison ivy, minor burn wounds, and other minor skin irritations.

EXAMPLE 2

The following ingredients were incorporated into the anesthetic lotion of this invention.

| Ingredient | Grams per 2.0 kilograms |
| --- | --- |
| Benzocaine, USP Micronized | 400 |
| Avicel RC 591 brand of sodium carboxymethyl cellulose | 40.0 |
| Solulan 16 brand of lanolin derivative | 2.0 |
| Methylparaben, NF | 4.0 |
| Propylparaben, NF | 0.5 |
| Aloe Vera Gel | 2.0 |
| Water q.s. to | 2000 grams |

The ingredients were admixed in accordance with the following procedure.

The methylparamen and propylparaben were dissolved in 100 grams of water contained in a jacketed kettle equipped with a propeller mixer and heated to 80° C. The aloe was added with mixing until dissolved. The Solulan 16 brand of lanolin derivative was added with mixing until dispersed. The dispersion containing the water, parabens, aloe and lanolin derivative was then added to a one gallon Waring Blender containing 500 grams of additional water. The Avicel brand of sodium carboxymethyl cellulose was added with the blender operating and then the benzocaine was added. The balance of the water was added with good mixing. The lotion contained about 20% by weight of benzocaine and is useful where a rapid onset of action is desired.

EXAMPLE 3

The following ingredients were incorporated into the anesthetic lotion of this invention.

| Ingredient | Grams per 2.0 kilograms |
| --- | --- |
| Benzocaine, USP Micronized | 400 |
| Avicel RC 591 brand of sodium carbixymethyl cellulose | 40.0 |
| Solulan 16 brand of lanolin derivative | 2.0 |
| Menthol, USP | 10 |
| Methylparaben, NF | 4.0 |
| Propylparaben, NF | 0.5 |
| Aloe Vera Gel | 2.0 |
| Carbomer 934 P brand of carboxy-vinyl polymer | 0.49 |
| Water q.s. to | 2000 grams |

The ingredients were admixed in accordance with the procedure of Example 1 except that the menthol was added to the dissolved parabens at a temperature of about 50° C. Again the lotion contained about 20% by weight of benzocaine.

EXAMPLE 4

The following ingredients were incorporated into the anesthetic lotion of this invention.

| Ingredient | Grams per 2.5 kilograms |
| --- | --- |
| Benzocaine, | 500 |
| Solulan 16 brand of lanolin derivative | 2.5 |
| Avicel-RC brand of Sodium carboxymethyl cellulose | 5.0 |
| Menthol | 12.5 |
| Methylparaben | 5 |
| Propylparaben | .625 |
| Simethicone, USP | 2.5 |
| Aloe Vera Oil | 2.5 |
| Water q.s. to | 2500 |

Water in the amount of 1960 grams was placed into a 3 liter jacketed stainless steel container equipped with a propeller type mixer and heated to 80° C. The methylparaben and propylparaben were added and mixed until dissolved. The sodium carboxymethyl cellulose was added and mixed at high speed for 10 minutes. The admixture was cooled to about 40° C. and the aloe, lanolin derivatives and menthol were then added in sucession. The benzocaine was then added slowly with mixing until completely dispersed. The remaining water was added with mixing. The mixture was processed through a homogenizer at 1000–1500 psig and filled into 3 ounce polypropylene bottles.

EXAMPLE 5

The following ingredients were incorporated into an anesthetic lotion of this invention.

| Ingredient | Grams per 1.5 kilograms |
| --- | --- |
| Benzocaine, USP Micronized | 120 |
| Solulan 16 brand of lanolin derivative | 2.0 |
| Menthol, USP | 7.5 |
| Methylparaben, NF | 3.0 |
| Propylparaben, NF | 0.3 |
| Aloe Vera Gel | 1.5 |
| Carbomer 934 P brand of carboxy-vinyl polymer | 7.5 |
| Sodium Hydroxide, q.s. to pH | 5.2 |
| Water q.s. to | 1500 grams |

The ingredients were admixed in accordance with the following procedure.

The methylparaben and propylparaben were dissolved in 1300 grams of water contained in a jacketed kettle equipped with a propeller mixer and heated to 80° C. The Carbomer 934 P brand of carboxy-vinyl polymer was added with the blender operating. The glyceryl monostearate was melted in a separate vessel and the melt added to the mixture in the kettle. The Solulan 16 brand of lanolin derivative was added with mixing until dispersed. The mixture was cooled to 40° C. and the micronized menthol mixed with the aloe oil was added to the kettle. The mixture was cooled to room temperature and the micronized benzocaine added followed by the sodium hydroxide and the remainder of the water. The mixture was then passed through a homogenizer at 1000 psig.

EXAMPLE 6

The ingredients and procedure of Example 5 are followed except that 0.150 grams of Yellow Ochre dye are added to the glyceryl monostearate after melting and thoroughly mixed before being added to the kettle. A very uniform yellow mixture resulted.

EXAMPLE 7

The following ingredients are incorporated into an anesthetic ointment as follows:

| Ingredient | Percent by weight |
|---|---|
| Benzocaine, USP, Micronized | 20 |
| Benzethonium Chloride | 0.1 |
| Menthol | 0.5 |
| Carbomer 934 P brand of carboxy-vinyl polymer | 1.5 |
| Trolamine | 0.3 |
| Shark liver oil | 1.5 |
| Water, chlorinated q.s. to | 100 |

Procedure

1. Add approximately 65% of the quantity of water to a container equipped with a high shear mixer and sweeps.
2. Add the carboxy-vinyl polymer and mix until homogenous.
3. Add shark liver oil, menthol, and benzethonium chloride and mix until homogenous.
4. Add benzocaine and mix until homogenous.
5. Add trolamine and mix until homogenous.
6. Balance formula with water and mix until homogenous.
7. Homogenize at 800 to 1000 psig.
8. Package in laminated tubes.

EXAMPLE 8

The following ingredients are admixed to form a gel composition in accordance with the invention.

| Ingredients | Percent by weight |
|---|---|
| Benzocaine, USP, Micronized | 20 |
| Menthol | 0.5 |
| Benzalkonium Chloride | 0.02 |
| Potassium Alginate | 2.5 |
| Cellulose Gum | 0.5 |
| Hamamelis Water q.s. to | 100 |

Mix and make a gelled suspension as follows:

Procedure

1. Add approximately 70% of the quantity of hamamelis water to a suitable container equipped with a high shear mixer and sweeps.
2. Heat the water to 50° C. and slowly add the cellulose gum with the mixers operating.
3. Add the potassium alginate slowly and mix until homogenous.
4. Pass the menthol through a 20 mesh screen to create a powder and add the powdered menthol to the batch and mix until homogenous.
5. Add the benzalkonium chloride to the batch and mix until homogenous.
6. Add the benzocaine to the batch and mix until homogenous.
7. Balance the formula to weight with hamamelis water and mix until homogenous.
8. Pass the batch through a homogenizer at 1000–1200 psig.
9. Package in plastic squeeze bottles.

The gel formulation of this example can be packaged and used as a teething aide, as a remedy to be applied to cold sores, insect bites and the like.

We claim:

1. A topical anesthetic composition containing high concentrations of benzocaine consisting essentially of 30–90% by weight of water and about 2 to about 20% by weight of benzocaine substantially in micronized form suspended in an admixture of the water and an emollient vehicle, the benzocaine solubility in the emollient vehicle being not greater than 2% by weight of benzocaine and the pH of the composition being in the range of 5 to 7.5.

2. The composition of claim 1 wherein the composition is a lotion.

3. The composition of claim 1 wherein the composition is an ointment.

4. The composition of claim 1 wherein the composition is a gel.

5. The composition of claim 1 wherein the emollient vehicle is selected from at least one member of the group consisting of lanolin and lanolin alcohol fractions, cetyl alcohol, lactates, glycerin, glyceryl monostearate, glyceryl monooleate, mineral oil, petrolatum, paraffin, and beeswax.

6. A topical anesthetic composition containing high concentrations of benzocaine consisting essentially of 30% to 90% by weight of water and about 8% to about 20% by weight of benzocaine substantially in micronized form having an average particle size not greater than 20 microns suspended in an admixture of the water and an emollient vehicle, the benzocaine dissolved in the emollient vehicle being not greater than 2% by weight of benzocaine and the pH of the composition being in the range of 5 to 7.5.

7. The composition of claim 6 wherein the composition is a lotion, the benzocaine content is about 8% by weight of benzocaine and the emollient vehicle consists essentially of lanolin alcohol fractions, glycerin and glycerol monostearate.

* * * * *